United States Patent [19]
Hori et al.

[11] Patent Number: 5,941,818
[45] Date of Patent: Aug. 24, 1999

[54] ENDOSCOPIC VIDEO CAMERA WITH MALLEABLE SUPPORT

[75] Inventors: Koichiro Hori, Framingham; Philip R. Lichtman, Newton, both of Mass.

[73] Assignee: Vista Medical Technologies, Inc., Carlsbad, Calif.

[21] Appl. No.: 08/722,742

[22] Filed: Oct. 1, 1996

[51] Int. Cl.⁶ .................................................. A61B 1/05
[52] U.S. Cl. .......................... 600/143; 600/114; 600/110
[58] Field of Search .................................... 600/101, 102, 600/112, 109, 114, 120, 136, 143

[56] References Cited

U.S. PATENT DOCUMENTS

| | | | |
|---|---|---|---|
| 4,607,622 | 8/1986 | Fritch et al. | 600/143 |
| 4,616,631 | 10/1986 | Takahashi | 600/139 |
| 4,727,416 | 2/1988 | Cooper et al. | 600/126 |
| 4,800,870 | 1/1989 | Reid, Jr. | 600/143 |
| 4,832,003 | 5/1989 | Yabe . | |
| 4,862,873 | 9/1989 | Yajima et al. . | |
| 4,867,137 | 9/1989 | Takahashi . | |
| 4,873,572 | 10/1989 | Miyazaki et al. . | |
| 4,947,827 | 8/1990 | Opie, deceased et al. | 600/153 |
| 5,008,793 | 4/1991 | Copeland . | |
| 5,033,528 | 7/1991 | Volcani . | |
| 5,122,650 | 6/1992 | McKinley . | |
| 5,166,787 | 11/1992 | Irion . | |
| 5,191,203 | 3/1993 | McKinley . | |
| 5,209,562 | 5/1993 | Glassford . | |
| 5,222,477 | 6/1993 | Lia . | |
| 5,327,881 | 7/1994 | Greene | 600/120 |
| 5,489,256 | 2/1996 | Adair | 600/133 |
| 5,513,827 | 5/1996 | Michelson . | |
| 5,607,094 | 3/1997 | Clark et al. | 227/175.1 |

OTHER PUBLICATIONS

"Desktop Color Video Camera For Scientific Applications", FlexCam Scientific; Videolabs, undated.

Wood et al., "Stereoendoscopy Gives Surgeons Normal Vision", Photonics Spectra, Sep. 1993.

*Primary Examiner*—John P. Leubecker
*Attorney, Agent, or Firm*—Pandiscio & Pandiscio

[57] ABSTRACT

An endoscope is provided that comprises a micro-size video camera, a flexible cable attached to the camera comprising fiber optical means for transmitting light to illuminate the site viewed by the camera and electrical conductors for transmitting electronic signals generated by the camera in response to images viewed by the camera, and a malleable or rigid shaft detachably connected to and supporting said camera and said cable. The rigid shaft may be straight or may be preformed in a selected curved configuration. In an alternative embodiment of the invention, a malleable shaft is permanently attached to said camera. Using a malleable shaft offers the advantage that the shaft is manually manipulable into various configurations to facilitate access to different surgical sites, with the shaft having the ability to remain in each selected configuration until manually reformed into another configuration. Using a detachable shaft provides the advantage that different shafts may be used with the same camera to provide different endoscope configurations for different applications.

21 Claims, 5 Drawing Sheets

ENDOSCOPIC VIDEO CAMERA WITH MALLEABLE SUPPORT

BACKGROUND OF THE INVENTION

1. Field of the Invention

This invention relates to surgical instruments and is directed more particularly to endoscopes by which surgical sites may be viewed by the operating physician.

2. Description of the Prior Art

Endoscopes, which are instruments used to inspect cavities or openings or selected sites, have found a number of applications in medicine and other technologies. In the field of medicine, the use of endoscopes permits inspection of organs or tissue for the purpose of facilitating the obtainment of biological specimens or the viewing of a surgical site for the purpose of facilitating the manipulation of other surgical instruments so as to avoid invasive and traumatizing surgical procedures.

Endoscopes generally comprise an insertion portion that is designed to be inserted into a patient. Older conventional endoscopes used in medicine contain an objective lens unit at the distal (forward) end of the insertion portion which transmits an image of the area forward of the objective lens unit to a remote eye-piece for viewing by the surgeon, the image being transmitted to the eye-piece via an image forwarding means in the form of a relay lens set, or an optical fiber bundle unit. In more recent years, in place of the eye-piece and at least part of the image forwarding means, it has been preferred to provide a small size solid state video imaging device, such as one constituting a CCD chip, in the imaging plane of the objective lens, and applying the output of that video imaging device via a suitable electronic transmission system to a video monitor for viewing by a user. The combination of an objective lens and a solid state video imaging device constitutes a video camera. With both types of image transmitting and viewing arrangements, a surgeon can view the displayed image and use the information conveyed by that image to manipulate the endoscope and also other surgical instruments that have been inserted into the patient via another incision or opening in the patient's body.

Video endoscopes also may be of the stereo variety, comprising optical means for generating first and second optical images, and video imaging means for generating first and second electrical signals in response to the first and second optical images respectively. The present state of the art of endoscopes prior to this invention is demonstrated by various U.S. and foreign patents ands also pending patent applications. By way of example, the present state of the art is demonstrated by the following U.S. patent applications: (1) Ser. No. 08/286543, filed Aug. 5, 1994 by K. Hori; (2) Ser. No. 08/319,886, filed Oct. 7, 1994 by K. Hori et al; (3) Ser. No. 08/475,364, filed Jun. 7, 1995 by K. Hori et al, and (4) Ser. No. 08/545297, filed Oct. 20, 1995 by K. Hori et al; Those patent applications show and describe optical, electronic and mechanical components of a contemporary endoscope. The teachings of those patent applications are incorporated herein by reference thereto.

The insertion portions of conventional endoscopes usually have a generally rigid tubular construction but in some endoscopes the invention portion comprises a flexible tubular construction. In many instances, such constructions are consistent with the desired use of the endoscope. However, in some instances, as in some by-pass heart surgery procedures, it would be helpful to the attending physician to be able to configure the insertion portion of the endoscope to a selected shape to facilitate proper positioning of the camera in the patient or in relation to the surgical incision, and to have that insertion portion retain that shape until changed by the physician. For example, in certain heart surgery procedures, incisions commonly are made between the fourth and fifth ribs. The fourth and fifth ribs are separated vertically and one of the ribs is displaced forwardly to provide a vertical opening for insertion of the endoscope, and related surgical instruments, between the rib cage and the heart. The endoscope usually is inserted from below and moved upwardly. Because there is little room between the rib cage and the heart, there is considerable difficulty in properly positioning an endoscope at the surgical site. It would be helpful to the physician to be able to configure the insertion portion of the endoscope in a manner advantageous for entry and positioning relative to the surgical site, and have the endoscope maintain that configuration until changed by the physician. It also would be of value to the surgeon to be able to position and use the video camera in different situations without being restricted by the physical construction of the insertion portion. A further consideration of this invention is that prior endoscopes have been designed for particular procedures and are not suitable for use in other procedures.

SUMMARY OF THE INVENTION

Accordingly, one primary object of the invention is to provide an endoscope having a video camera mounted on a malleable shaft which is manually configurable so as to facilitate access to a surgical site and is adapted to retain the selected configuration until manually shaped another configuration.

Another primary object is to provide an endoscope wherein the insertion portion comprises a video camera and a shaft supporting said camera that is detachable and replaceable.

A further object is to provide an endoscope having a novel insertion portion characterized by a monocular or stereo video camera.

With the above and other objects in view, as will hereinafter appear, a feature of the present invention is the provision of an endoscope comprising a micro size video camera, a shaft that supports the camera, and a flexible cable connected to the camera and carried by the shaft that comprises electrical wiring for image transmission and fiber-optic elements for illumination of a surgical site viewed by the camera. The electrical wiring for image transmission is in communication with a video controller that processes the electrical output of the video camera and is used to cause a monitor to display a video reproduction of the image seen by the camera, while the fiber-optic elements for illumination are connected to a light source. In a preferred embodiment of the invention the shaft is detachable from the cable and is malleable in the sense that it is manually reconfigurable into a selected shape that facilitates access to a selected surgical site and will remain in said selected shape until manually reconfigured to another shape. In another embodiment the shaft is detachable from the cable but has a predetermined configuration that may not be manually changed by the surgeon. In still another embodiment the shaft forms an integral unit with the camera (i.e., is not detachable) but is malleable so as to permit the surgeon to configure the shaft to a selected shape that he deems necessary or advantageous with respect to a particular surgical procedure.

The above and other features of the invention, including various novel details of construction and combinations of parts, will now be more particularly described with reference to the accompanying drawings. It will be understood that the several devices embodying the invention herein described are intended by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings.

Identical elements are identified by the same numerals in the several figures.

DESCRIPTION OF THE PREFERRED EMBODIMENTS

Figure 1:
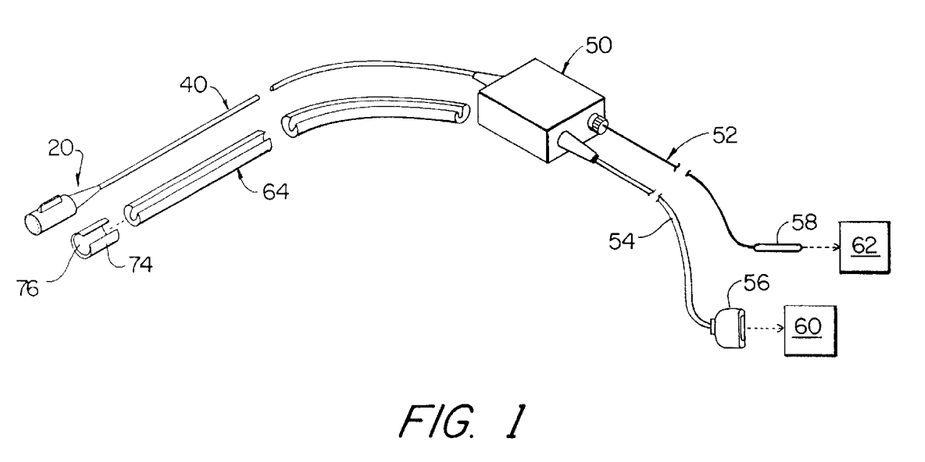
FIG. 1 is a perspective, partially exploded, view of an endoscope illustrative of one preferred embodiment of the invention.
Figure 2:
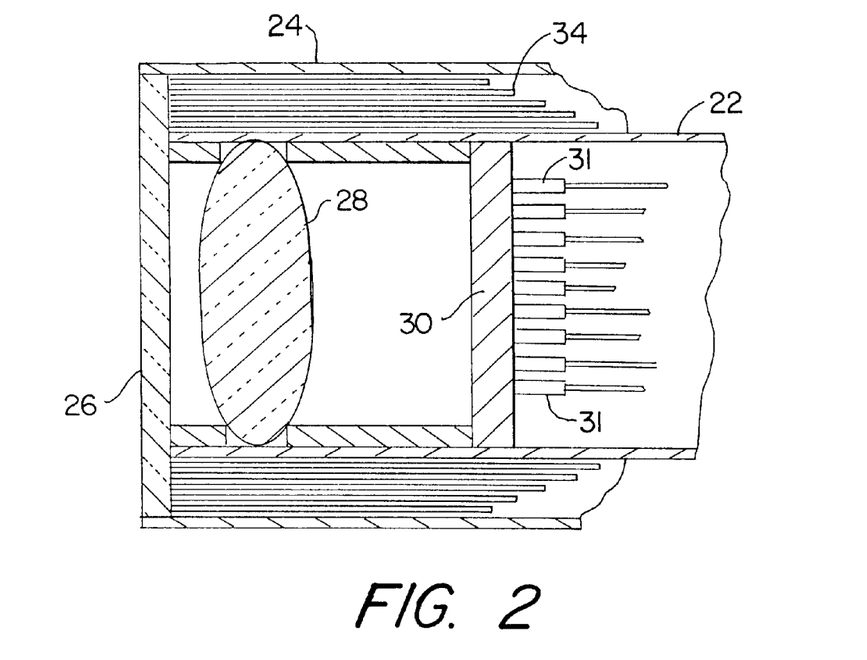
FIG. 2 is a sectional view in side elevation of a portion of the camera unit shown in FIG. 1.
Figure 3:
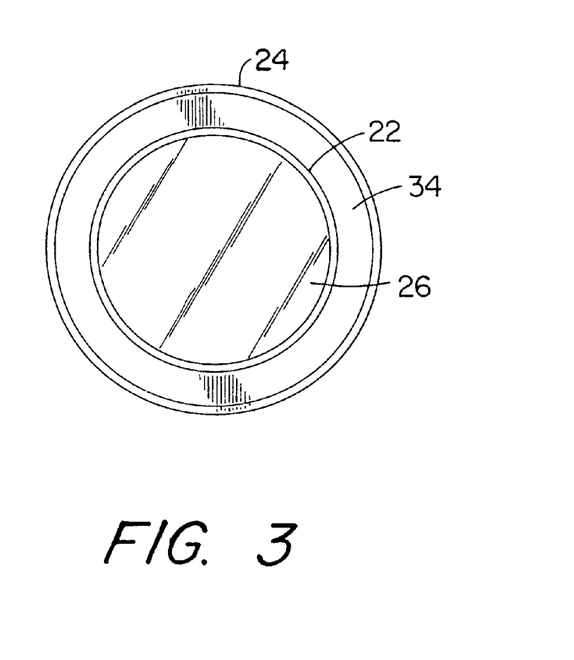
FIG. 3 is front end view in elevation of the same camera unit on an enlarged scale.
Figure 4:
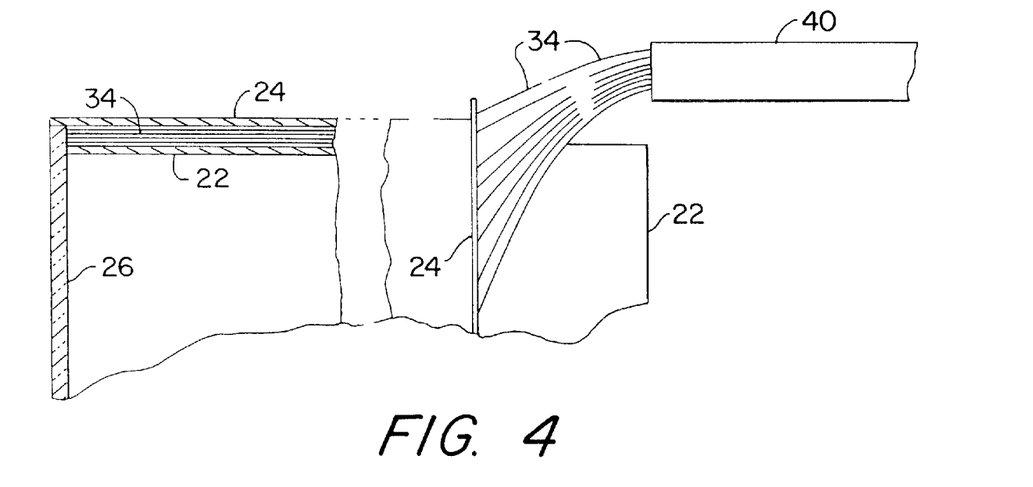
FIG. 4 is a fragmentary schematic side elevation, partly in section, showing how the bundle of optical fibers are spread out in entering the camera housing and how the fibers terminate at the distal end of the camera unit.

FIG. 1 shows an endoscope system that comprises a small video camera 20 which may be a monocular camera or a stereo camera. In this particular embodiment the camera unit is a monocular camera which, as seen in FIGS. 2 and 3, comprises a pair of concentric tubes 22 and 24 preferably made of metal, a window 26 mounted within tube 22 at its front or distal end, an objective lens 28, and an electronic imaging device 30, preferably comprising a CCD chip, which is adapted to convert an optical image received from the objective lens assembly into electronic signals for use in forming a video image on a display monitor. The CCD ship has terminal pins 31 for connection to electrical conductors. The objective lens system is designed to collect or form an image of an area under inspection in front of window 26 and to focus that image on the light-receiving surface of the CCD. The objective lens system may comprise one or more lenses and its lens or lenses may, but need not, be contained in a protective tubular casing (not shown) that fits within and is anchored to inner tube 22. An optical image relaying means (not shown) may be utilized to relay the image from the objective lens onto the CCD chip, but for the purpose of minimizing the axial length of the camera unit and better realizing certain advantages of this invention, it is preferred that no optical relay means be employed, so that the image is transmitted directly from the objective lens onto the CCD chip.

The annular space between the two tubes 22 and 24 is occupied by a plurality of optical fibers 34 which serve the purpose of transmitting light to the region in front of window 26. Preferably the front ends of the optical fibers terminate in a common plane parallel to the plane of window 26, while the rear ends of the fibers protrude out from the rear or proximal ends of tubes 22 and 24 and form part of a cable assembly 40 (FIG. 1) hereinafter described. The two concentric tubes 22 and 24 and the forward (distal) portions of the optical fibers 34 form a discrete housing assembly that serves to contain window 26, objective lens 28 and imaging device 30.

A camera unit having an objective lens and an electronic imaging device is not novel, being described and/or illustrated, for example, in U.S. Pat. Nos. 4,873,572, 4,862,873, 4,873,572 and 5,832,003, and U.S. patent application Ser. No. 08/319,886, filed Oct. 7 1994 by Koichiro Hori et al.

Figure 6:
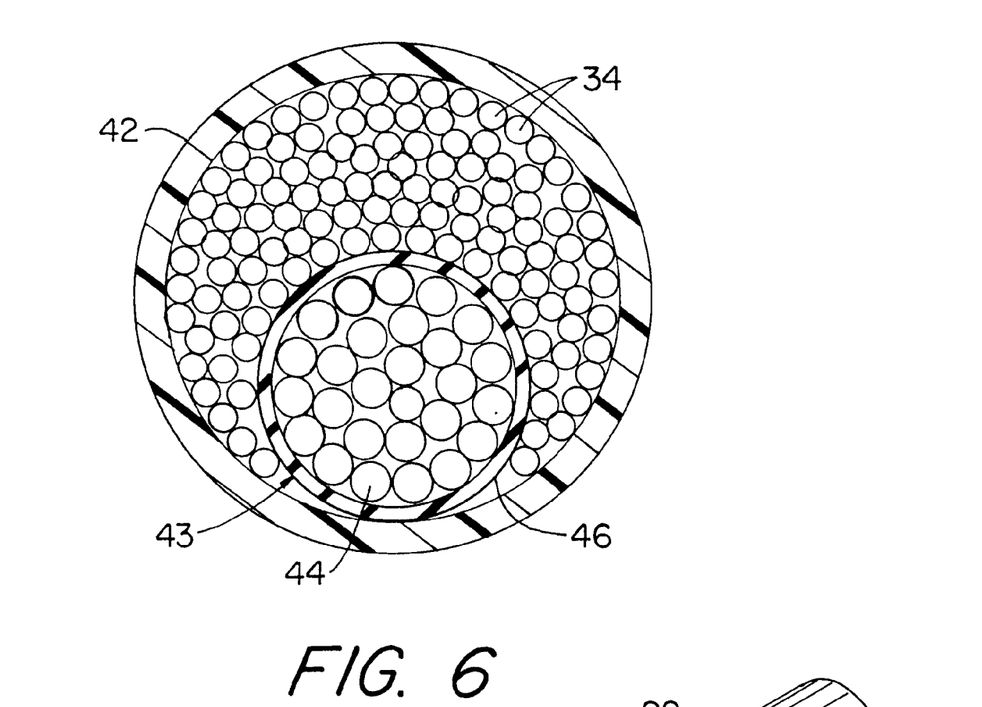
FIG. 6 is a cross-sectional view of the cable that is attached to the support shaft shown in FIGS. 1 and 5.

Referring now to FIGS. 1 and 6, attached to the camera unit at its rear or proximal end is a flexible cable 40 that comprises an outer insulating sheathing 42, the optical fibers 34 and an electrical cable 43 that comprises in turn a plurality of electrical conductors 44 encased in a flexible sheath or casing 46 that is made of an electrically-insulating material, e.g. a plastic such as polyethylene. It should be noted that FIG. 6 is illustrative only and that the number of electrical conductors and optical fibers may be more or less than what is shown in that figure.

The proximal end of cable 40 is attached to a connector box 50 (FIG. 1) where the optical fibers 34 and the electrical cable 43 are connected to a flexible light guide cable 52 and a camera cable 54. Light guide cable 52 preferably comprises a single relatively large diameter optical fiber encased in a protective flexible sheath and the camera cable 54 comprises a number of electrical conductors encased in a protective flexible sheath. Each of the electrical conductors of camera cable 54 is connected to a different one of the electrical conductors that make up the electrical cable 43. The proximal end of camera cable 54 is connected to a multi-pin plug-in type electrical connector 56 while the proximal end of light guide cable 52 is connected to a plug-in type light guide connector 58. Connector 56 is used to connect the camera cable to a video controller 60 that is adapted to receive the video signals generated by the CCD and utilize same to generate a video image on a video monitor (not shown). The connector 58 is used to connect light guide cable 52 to a suitable light source 62.

Figure 5:
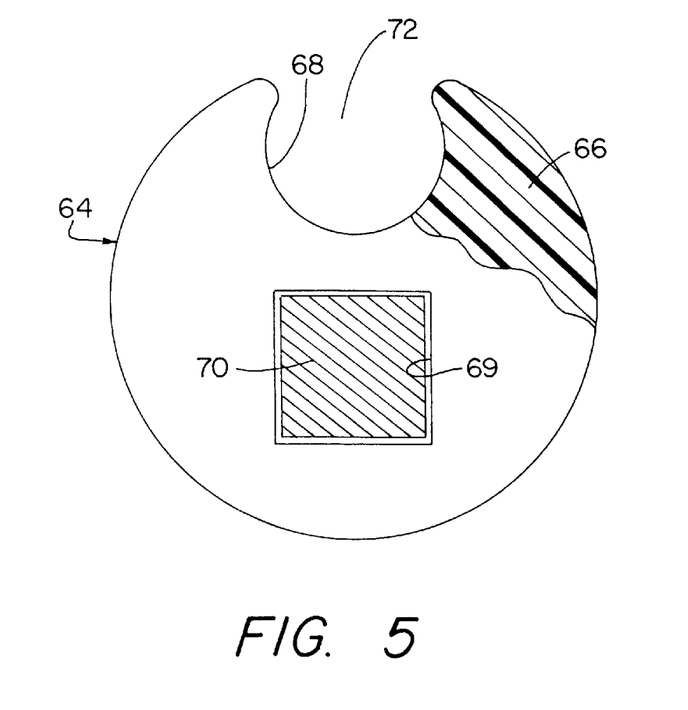
FIG. 5 is an end view of the support shaft, with a portion of the support shaft being shown in section.

In accordance with this invention, the cable 40 is releasably attached to a separate elongate support member 64 that is hereinafter identified as the "support shaft". Referring now to FIGS. 1 and 5, support shaft 64 comprises an elongate rod 66 that preferably, but not necessarily, has a generally cylindrical shape in cross-section, except that it is provided with an axially extending surface groove 68 for receiving cable 40. In this preferred embodiment support shaft 64 is malleable in the sense that it can be bent manually to a selected shape and will retain that shape until it is reformed manually to its original or a different shape. Accordingly rod 66 is made of an elastomeric material having embedded in an axial bore 69 thereof an axially extending elongate metal wire or rod 70 that is malleable in the sense that it is capable of being reformed from one shape to another, and of retaining a selected shape until reformed to another shape. Preferably these requirements are met by making rod 70 of a "dead soft" metal. As used herein the term "dead soft" means that the metal is capable of being bent to a particular shape and of holding that shape until it is reformed to a new shape or back to its original shape. Preferably rod 70 comprises lead or dead soft aluminum. It should be noted that in FIG. 5, the gap between rod 70 and the bore 69 is exaggerated for purposes of illustration and that in practice rod 70 makes a tight fit in bore 69 and may be bonded to rod 66.

Groove 68 has a generally circular curvature in cross-section, terminating at the surface of rod 66 in a narrow elongate opening 72. The diameter of groove 68 is only slightly larger than that of cable 40, while the narrow opening 72 has a width less than the diameter of cable 40. Accordingly cable 40 can make a snap fit in groove 68, with the difference in size between the smaller diameter of groove 68 and the outer larger diameter of cable 40 being small enough to assure that cable 40 is tightly gripped by the support shaft.

Shaft 64 is releasably coupled to camera 20 by means of a spring clip 74 in the form of a generally cylindrical sleeve that is split as shown at 76 so as to allow it to be forced onto the camera and shaft 64. The clip is sized that that it can accept and make a tight gripping connection with the camera and shaft 64, with the forward half of the clip releasably gripping camera 20 and the rearward half of the clip releasably gripping the forward end portion of support shaft 64. A similar clip (not shown) may be used to attach shaft 64 to a tubular extension (not shown) on connector box 50.

In the embodiment of FIG. 1 the malleable shaft 64 not only acts as a support for the camera but also offers the advantage that it can be bent into a selected shape as may be required by the surgeon for a particular procedure and will hold that shape until it is manually reformed into a new shape or its original shape.

Of course, it is also contemplated that support shaft 64 may be non-malleable, i.e., made of a material that can be preformed to a particular shape and cannot be reformed into another shape that it is capable of retaining. For example, support shaft 64 may be made of a metal or plastic material that is preformed into a particular shape, e.g., a straight or curved shaft and is not capable of being manually bent, without additional heat or other treatment, into a new shape and retaining that shape. In such case the support shaft may consist of just rod 66. Alternatively support shaft 64 may have the same construction as the embodiment of FIG. 1, except that the wire or rod 70 is made of a material that cannot be bent into a new shape and retain that new shape. That requirement is met by using a rod 70 that is rigid and made of stainless steel or other suitable material, or by using a rod 70 made of a spring metal, e.g., spring steel. Regardless of whether the rod 70 is rigid or made of a spring steel, it may be formed initially as a straight member or as a member having a selected curved shape.

Whether the support shaft is malleable or non-malleable, the preferred embodiment of the invention offers the advantage that the support shaft is removable. Additionally, if the support shaft is malleable, it may be reshaped more than once and hence it offers the advantage of being reusable. If the support shaft is not malleable, the fact that it is still removable offers the advantage that it can be replaced by another shaft having the same or a different shape.

Figure 7:
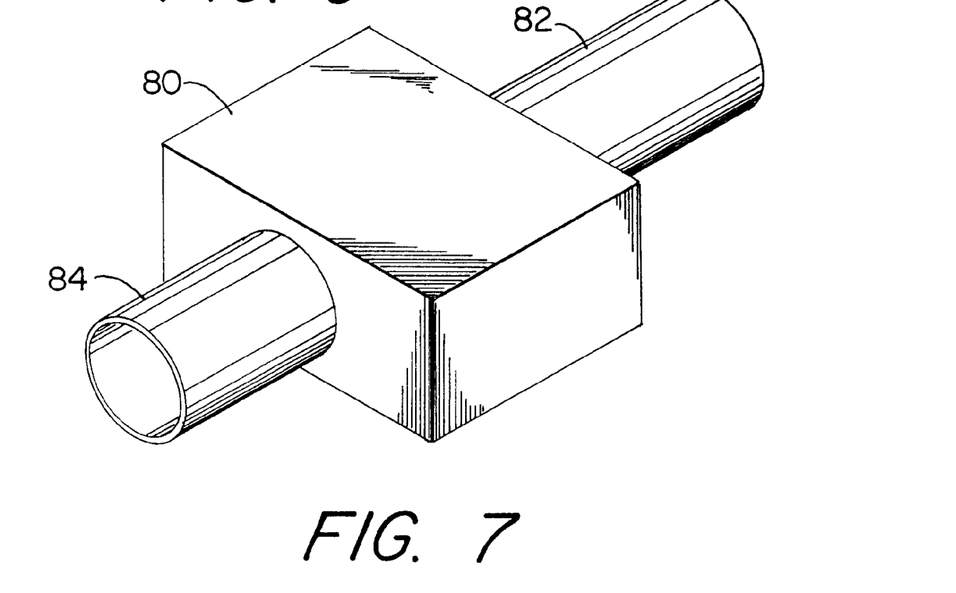
FIG. 7 is perspective view of a stereo camera that can be used in place of the monocular camera of FIG. 1.

The invention is also useable with stereo video cameras. FIG. 7 shows one form of stereo video camera that may be used with the present invention. In this case the video camera comprises a housing 80 having a tubular rear or proximal extension 82 and a tubular front or distal extension 84. Housing 80 contains two solid state imaging devices (not shown) disposed side by side. Tubular extension 82 provides an entry port to the housing for the combined optical fibers/electrical wire cable 40, while the extension 84 serves as a casing that houses the optics portion of the camera, with or without a front window like window 26. Tubular extension 84 has a dual tube construction similar to that provided by tubes 24 and 26 (FIGS. 1–3) with the glass fibers 36 of cable 40 filling the annular space between the two concentric tubes.

Although not shown, it is to be understood the optics of the stereo video camera contained in distal extension 84 may consist of two objective lens units mounted side by side so that each provides a separate image of the viewed area in front of the camera. Alternatively the camera may comprise a single objective lens mounted in tubular extension 84 that is designed so as to be capable of providing two separate stereo images. Stereo arrangements that employ two objective lenses are shown by Wood et al, "Stereoendoscopy Gives Surgeons Normal Vision", Photonics Spectra, pp. 40–43, September 1993, and by U.S. Pat. Nos. 4,873,572 and 4,862,873. The single objective lens stereo arrangement also is well known, being shown, for example, by U.S. Pat. Nos. 5,122,650 and 5,191,203, both issued to Harry R. McKinley. As already noted, the housing 80 serves to contain two video imaging devices, e.g., two CCD units (not shown). These two imaging devices are arranged so that one receives a first one of the two optical stereo images and the other receives the second of the two optical stereo images. The two imaging devices produce first and second electrical signals representative of and in response to the first and second images respectively that they receive. Those first and second electrical signals are carried by electrical cable 44 back to a video controller 60 where they are processed and used to provide a display on the video monitor (not shown).

Figure 8:
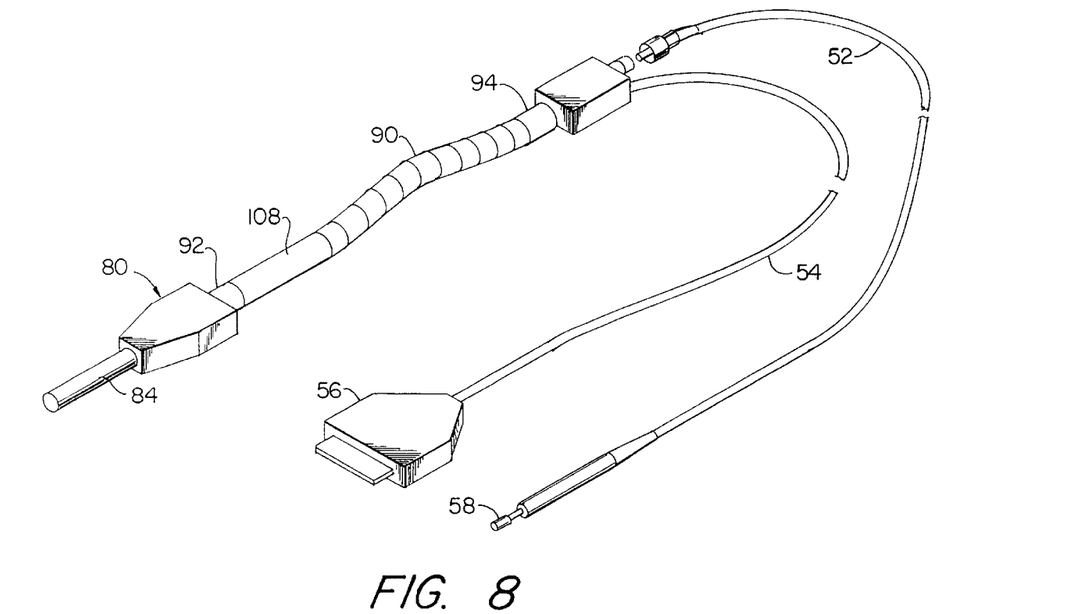
FIG. 8. is a perspective view of another alternative embodiment of the invention.
Figure 9:
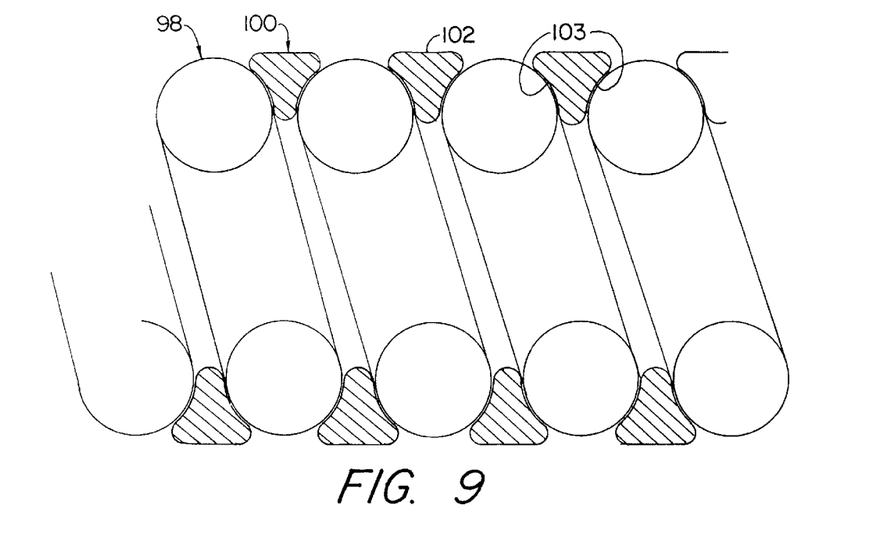
FIG. 9 is a center-line sectional view in elevation of a gooseneck shaft that forms part of the embodiment of FIG. 8.

FIGS. 8 and 9 show another endoscope having a malleable shaft. However, in this case the shaft is permanent and functions as a flexible protective conduit for the cable 40. As illustrated in FIGS. 8 and 9, this embodiment utilizes the stereo camera described above in connection with FIG. 7. However, it is to be understood that the stereo camera may be replaced by the monocular video camera as shown in FIGS. 1–3. In this case the cable 40, containing both the optical fibers 36 and electrical cable 44, is encased in a flexible gooseneck conduit 90, with one end of the conduit being attached to the tubular extension 82 of the camera by a first ferrule connector 92 and the other end of the conduit being attached to the connector box 50 by a second ferrule connector 94. The gooseneck conduit may take various forms known to persons skilled in the art. See, for example the gooseneck constructions shown by U.S. Pat. Nos. 5,008, 793, 5,033,528, 5,209,562, and 5,513,827.

Preferably, however, the gooseneck conduit comprises a helical (coiled) spring 98 (FIG. 9) made of a metal wire that is circular in cross-section, and another helical member 100 that surrounds and is interfitted with the turns of spring 98. The outer helix is made of a metal wire that is generally triangular in cross-section, with one side surface 102 of that cross-section being flat and the other two side surfaces 103 having a concave circular curvature sized so that they will make a close fit with portions of the surfaces of adjacent turns of spring 98. The turns of spring 98 are separated from their normal spacing by the turns of helical member 100, with the latter making a tight frictional fit with the turns of coil spring 98, with the result that the two helical members operate in unison to provide malleability to the conduit. In its as-formed state the conduit is straight. However, the foregoing construction allows the conduit to be bendable lengthwise (as the term "gooseneck" implies), and if the conduit is bent to a desired shape, the friction between the two helical members causes them to remain in that bent shape. The conduit is completed by provision of a flexible electrically-insulating tubular covering or sheath 108 (only a portion thereof is shown in FIG. 8), which preferably is made of a suitable plastic such as polyethylene and extends along the length of helical members 98 and 100.

There is thus provided an endoscope which can be bent to a selected configuration to facilitate insertion thereof into a patient and which will remain in that selected configuration until changed by the operating physician.

By way of example but not limitation, an endoscope as illustrated in FIG. 1 is characterized by the following specification: (1) field of view=500; (2) object distance=6 cm. minimal; viewing angle=0° straight; maximum outer diameter ("o.d.") of camera=8.5 mm; light source to connector box is a single 780 micron fiber; length of support shaft=approximately 12 inches measured between camera and connector box.

It is to be understood that the present invention is by no means limited to the particular constructions herein disclosed and/or shown in the drawings, but also comprises any modifications or equivalents within the scope of the following claims.

We claim:

1. An endoscope comprising:
   a video camera having a housing with a distal end and a proximal end, said camera also including within said housing optical means for acquiring images of objects and electronic imaging means for producing electrical signals representative of said images;
   a flexible cable connected to said video camera, said cable including fiber optic means for transmitting light to the area in front of said distal end of said camera and electrical conductors connected to said electronic imaging means for carrying said electrical signals from said camera to apparatus for processing said signals and generating therefrom a video display of the image seen by said camera; and
   a malleable shaft having distal and proximal ends with said distal end being attached to said camera housing, said shaft also having a groove in its outer surface, with said cable being disposed in said groove in secured relation with said shaft, whereby said shaft acts to carry and support said cable.

2. An endoscope according to claim 1 wherein said cable extends lengthwise beyond the proximal end of said shaft.

3. An endoscope according to claim 1 wherein said cable is releasably secured to said shaft by a tight fit in said groove.

4. An endoscope according to claim 1 wherein said shaft comprises a rod of elastomeric material and a malleable metal wire embedded in and extending lengthwise along said rod.

5. An endoscope in accordance with claim 4 wherein said wire is made of aluminum or lead.

6. An endoscope in accordance with claim 1 wherein said distal end of said shaft is releasably attached to said camera housing by a spring clip that is mounted on the distal end of said shaft and frictionally embraces said housing.

7. An endoscope in accordance with claim 1 wherein said optical means comprises an objective lens, and said housing is characterized by first and second tubular members with said first tubular member surrounding said second tubular member and said second tubular member surrounding said objective lens, and said fiber optic means for transmitting light comprises a plurality of optical fibers having first and second opposite ends, with said first ends being disposed between said first and second tubular members.

8. An endoscope according to claim 1 wherein said camera is a stereo camera.

9. An endoscope comprising:
   a video camera comprising a free-standing housing having a tubular extension characterized by first and second tubular members with said first tubular member surrounding said second tubular member, means including an objective lens mounted within said second tubular member for acquiring optical images of objects in the field of view of the camera, and solid state imaging means mounted within said housing for receiving the optical images acquired by said optical means and producing electrical signals representative of said optical images;
   a malleable hollow shaft having proximal and distal ends, with said distal end being secured to said camera housing;
   a flexible cable disposed within said shaft, said cable comprising electrical conductors for image transmission connected to said solid state imaging means and fiber-optic lines for illumination of a surgical site extending between said first and second tubular members;
   said electrical conductors for image transmission also being in communication with a camera control means that is adapted to receive said electrical signals via said electrical conductors and generate from said signals video image signals for operating a video display means;
   said fiber-optic lines for illumination being connected to a light source; and
   the shape of said shaft being manually reformable so that (a) it may be configured to a selected shape to facilitate access to a surgical site and (b) will remain in said selected shape until manually reformed to another shape.

10. An endoscope in accordance with claim 9 wherein said shaft comprises a first helical coil member defining a passageway for said cable, and a second helical coil member surrounding said first helical coil member.

11. An endoscope in accordance with claim 10 wherein said cable further includes an electrically-insulating sheath covering said electrical conductors and said fiber optic lines.

12. An endoscope comprising:
   a video camera comprising a housing containing optical means for acquiring optical images of an object in the field of view of the camera and electronic imaging means for receiving said optical images and producing electrical signals representative of said images;
   a malleable shaft having proximal and distal ends, with said distal end being releasably connected to said camera housing, said shaft having a longitudinally-extending groove in its outer surface;
   a flexible cable positioned with and extending lengthwise of said groove, said cable being releasably secured to said shaft by a friction fit in said groove, said cable having a distal end and a proximal end and comprising electrical conductors for image transmission and fiber-optic lines for illumination of a surgical site, said cable being fixed at a distal end thereof to said camera so that said electrical conductors are connected to said electronic imaging means and said fiber optic lines are arranged to transmit light to illuminate the field of view of the camera;

said cable extending lengthwise of said shaft and terminating beyond the opposite ends of said shaft; and connector means attached to the proximal end of said cable for connecting said conductors to an external circuit for processing the electrical signals produced by said electronic imaging means and said fiber-optic lines to a light source, said connector means being independent of said shaft;

said shaft being malleable in the sense that it may be manually bent into a selected configuration for access to a surgical site and will retain such selected configuration until bent into another configuration.

13. The endoscope in accordance with claim 12 wherein said cable includes a flexible electrically-insulating sheath surrounding said electrical conductors and said fiber optic lines.

14. An endoscope in accordance with claim 13 wherein said shaft comprises a rod of elastomeric material and a metal wire embedded in and extending lengthwise along said rod.

15. An endoscope in accordance with claim 14 wherein said metal wire is made of lead or aluminum.

16. An endoscope in accordance with claim 12 comprising a spring clip at said distal end of said shaft for releasably connecting said shaft to said camera housing.

17. An endoscope comprising:

a video camera comprising a free-standing housing containing an objective lens and electronic imaging means for producing electrical signals representative of the optical images acquired by said objective lens;

a plurality of electrical conductors connected to said electronic imaging means for transmission of electronic signals produced by said camera that are representative of the optical image sensed by said camera, and a plurality of optical fibers extending into said housing for transmitting light to the optical sight viewed by said objective lens;

connector means for connecting said electrical conductors to means for processing the electronic signals generated by said electronic imaging means and connector means for connecting said optical fibers to a light source; and a hollow shaft attached to said housing and surrounding and supporting said electrical conductors and said optical fibers, said shaft comprising a pair of concentric flexible and resilient coils and being flexible and malleable in the sense that said shaft can be bent manually to a selected shape and will hold that shape until it is bent manually to another selected shape, and a flexible electrically-insulating sheath surrounding and covering said shaft.

18. An endoscope comprising:

a video camera having a free-standing housing with a distal end and a proximal end, said camera also including within said housing optical means including an objective lens for acquiring images of objects and electronic imaging means for producing electrical signals representative of said images;

a flexible cable having a distal end extending into said housing, said cable including fiber optic means for transmitting light to the area in front of said distal end of said camera housing and electrical conductors connected to said electronic imaging means for carrying said electrical signals from said camera to apparatus for processing said signals and generating therefrom a video display of the image seen by said camera;

a malleable shaft having distal and proximal ends with said distal end being releasably attached to said camera housing, said shaft also having a longitudinally-extending groove in its outer surface, with said cable being disposed in said groove in a releasable connection with said shaft, whereby said shaft acts to carry and support said cable; and connector means attached to the proximal end of said cable independently of said shaft for connecting (a) said conductors to apparatus for processing said signals and generating therefrom a video display of the images seen by said camera, and (b) said fiber optic means to a light source.

19. An endoscope according to claim 18 wherein said camera is a stereo camera.

20. A micro-size camera apparatus comprising:

a free-standing housing with a distal end and a proximal end, said distal end having a window through which objects may be viewed;

optical means mounted within said housing for acquiring optical images of objects viewed through said window;

electronic imaging means mounted within said housing for receiving the optical images acquired by said optical means and for producing electrical signals representative of said acquired optical images;

a flexible cable having a distal end connected to said housing, said cable including fiber optic means for transmitting light to the area in front of said distal end of said camera housing and electrical conductors connected to said electronic imaging means for carrying said electrical signals from said camera to apparatus for processing said signals and generating therefrom a video display of the image seen by said camera;

a malleable shaft having distal and proximal ends with said distal end being releasably attached to said camera housing, said shaft also having a groove in its outer surface, with said cable being disposed in said groove in secured relation with said shaft, whereby said shaft acts to carry and support said cable; and connector means attached to the proximal end of said cable independently of said shaft for connecting (a) said conductors to apparatus for processing said signals and generating therefrom a video display of the images seen by said camera, and (b) said fiber optic means to a light source.

21. A micro-size camera apparatus comprising:

a free-standing housing having a distal end and a proximal end, said distal end having a window through which objects may be viewed;

optical means including an objective lens mounted within said housing for acquiring optical images of objects viewed through said window;

electronic imaging means mounted within said housing for receiving the optical images acquired by said optical means and producing electrical signals representative of said acquired optical images;

a flexible cable having a distal end and a proximal end, said cable comprising (a) electrical conductors connected at said distal end of said cable to said electronic imaging means for transmitting said electrical signals to apparatus for processing said signals and generating therefrom a video display of said acquired image, and (b) fiber-optic lines at said distal end of said cable connected to said housing for conducting light to illuminate objects viewed by said objective lens;

a hollow malleable shaft surrounding and supporting said cable, said shaft including an electrically-insulating outer surface and having proximal and distal ends with said distal end fixed to said housing, whereby said housing is supported by said shaft; and means attached to said proximal end of said shaft for releasably connecting said electrical conductors to an exterior circuit for processing said electrical signals and releasably connecting said fiber optic lines to a light source for providing light to illuminate said objects.

* * * * *